(12) United States Patent
Kwiatkowski (10) Patent No.: US 6,255,475 B1
(45) Date of Patent: Jul. 3, 2001

(54) CHAIN TERMINATORS, THE USE THEREOF FOR NUCLEIC ACID SEQUENCING AND SYNTHESIS AND A METHOD OF THEIR PREPARATION

(76) Inventor: Marek Kwiatkowski, Lövsångarvägen 17, S-756 52 Uppsala (SE)

( * ) Notice: Subject to any disclaimer, the term of this patent is extended or adjusted under 35 U.S.C. 154(b) by 0 days.

(21) Appl. No.: 08/875,243

(22) PCT Filed: Jan. 30, 1996

(86) PCT No.: PCT/SE96/00096

§ 371 Date: Sep. 16, 1997

§ 102(e) Date: Sep. 16, 1997

(87) PCT Pub. No.: WO96/23807

PCT Pub. Date: Aug. 8, 1996

(30) Foreign Application Priority Data

Jan. 31, 1995 (SE) ................................................. 9500342

(51) Int. Cl.[7] ............................. C07H 21/00; C07H 19/04
(52) U.S. Cl. .................. 536/25.3; 536/25.32; 536/25.34; 536/26.1; 536/26.2; 536/26.26
(58) Field of Search .................... 536/26.1, 25.3, 536/25.32, 25.34, 26.2, 26.26

(56) References Cited

U.S. PATENT DOCUMENTS 5,302,509  4/1994  Cheesman .

FOREIGN PATENT DOCUMENTS

| 0286028 | 10/1988 | (EP) . |
| 0399330 | 11/1990 | (EP) . |
| 0628568 | 12/1994 | (EP) . |
| 09106678 | 5/1991 | (WO) . |
| 09423064 | 10/1994 | (WO) . |

OTHER PUBLICATIONS

Sandstrom et al. Acta Chemica Scandinavica B 39, 273–290, 1985.*
Roberts and Caserio. Basic Principles of Organic Chemistry. W. A. Benjamin, Inc., New York: 1965, pp. 443–447.*
STN Intl., File CA, Chem. abs., vol. 24, Canard B.: "Catalytic editing properties of DNA polymerases", abs. No. 49135, & Proc. Natl. Acad. Sci. U.S.A. (1995), 92(24), 10859–63.

* cited by examiner

*Primary Examiner*—Gary L. Kunz
*Assistant Examiner*—Howard Owens
(74) *Attorney, Agent, or Firm*—Fish & Richardson P.C., P.A.

(57) ABSTRACT

The invention relates to compounds of general structure (I) or salts thereof, wherein B is a nucleobase, X and Z independently are oxygen or sulphur, Y is hydrogen or hydroxy, which optionally may be protected, $R_1$ is hydrocarbyl, which optionally is substituted with a functional group, $R_2$ is hydrogen or hydrocarbyl, which optionally is substituted with a functional group, A is an electron withdrawing or electron donating group capable of moderating the acetal stability of compound (I), $L_1$ and $L_2$ are hydrocarbon linkers, which may be the same or different, $L_2$, when present, being either (i) connected to $L_1$ via the group A, or (ii) directly connected to $L_1$, the group A then being connected to one of linkers $L_1$ and $L_2$, F is a dye label, Q is a coupling group for F, and l, m and n independently are 0 or 1, with the proviso that l is 1 when m is 1, and l is 1 and m is 1 when n is 1. The compounds of formula (I) are useful as deactivatable chain extension terminators. The invention also relates to the use of the compounds (I) in nucleic acid synthesis and nucleic acid sequencing as well as to a method of preparing compounds of Formula (I).

(I)

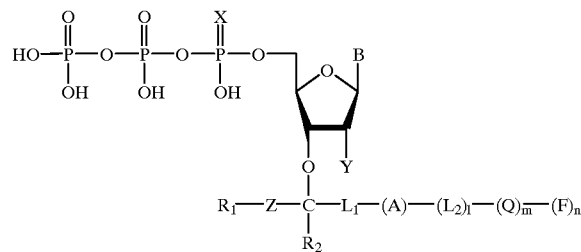

15 Claims, 5 Drawing Sheets

CHAIN TERMINATORS, THE USE THEREOF FOR NUCLEIC ACID SEQUENCING AND SYNTHESIS AND A METHOD OF THEIR PREPARATION

The present invention relates to novel nucleic acid chain extension terminators, their use in nucleic acid sequencing and synthesis, respectively, as well as a method for preparing such compounds.

Today, there are two predominant methods for DNA sequence determination: the chemical degradation method (Maxam and Gilbert, Proc. Natl. Acad. Sci. 74:560–564 (1977), and the dideoxy chain termination method (Sanger et al., Proc. Natl. Acad. Sci. 74:5463–5467 (1977)). Most automated sequencers are based on the chain termination method utilizing fluorescent detection of product formation. In these systems either primers to which deoxynucleotides and dideoxynucleotides are added are dye-labelled, or the added dideoxynucleotides are fluorescently labelled. As an alternative, dye labelled deoxynucleotides can be used in conjunction with unlabeled dideoxynucleotides. This chain termination method is based upon the ability of an enzyme to add specific nucleotides onto the 3' hydroxyl end of a primer annealed to a template. The base pairing property of nucleic acids determines the specificity of nucleotide addition. The extension products are then separated electrophoretically on a polyacrylamide gel and detected by an optical system utilizing laser excitation.

Although both the chemical degradation method and the dideoxy chain termination method are in widespread use, there are many associated disadvantages. For example, the methods require gel-electrophoretic separation. Typically, only 400–800 base pairs can be sequenced from a single clone. As a result, the systems are both time- and labor-intensive. Methods avoiding gel separation have been developed in attempts to increase the sequencing throughput.

Sequencing by hybridization (SBH) methods have been proposed by Crkvenjakov (Drmanac et al., Genomics 4:114 (1989); Strezoska et al., (Proc. Natl. Acad. Sci. USA 88:10089 (1991)), Bains and Smith (Bains and Smith, J. Theoretical Biol. 135:303 (1988)) and in U.S. Pat. No. 5,202,231. This type of system utilizes the information obtained from multiple hybridizations of the polynucleotide of interest, using short oligonucleotides to determine the nucleic acid sequence. These methods potentially can increase the sequence throughput beacuse multiple hybridization reactions are performed simultaneously. To reconstruct the sequence, however, an extensive computer search algorithm is required to determine the most likely order of all fragments obtained from the multiple hybridizations.

The SBH methods are problematic in several respects. For example, the hybridization is dependent upon the sequence composition of the duplex of the oligonucleotide and the polynucleotide of interest, so that GC-rich regions are more stable than AT-rich regions. As a result, false positives and false negatives during hybridization detection are frequently present and complicate sequence determination. Furthermore, the sequence of the polynucleotide is not determined directly, but is inferred from the sequence of the known probe, which increases the possibility for error.

Methods have also been proposed which detect the addition or removal of single molecules from a DNA strand. For example, Hyman E. D., Anal. Biochem., 174:423 (1988) discloses the addition of a nucleotide to a an immobilised DNA template/primer complex in the presence of a polymerase and determination of polymerisation reaction by detecting the pyrophosphate liberated as a result of the polymerisation.

Jett et al., J. Biomol. Struct. Dyn., I, p. 301, 1989 discloses a method wherein a single stranded DNA or RNA molecule of labelled nucleotides, complementary to the sequence to be determined, is suspended in a moving flow stream. Individual bases are then cleaved sequentially from the end of the suspended sequence and determined by a detector passed by the flow stream.

EP-A-223 618 discloses the use of an immobilised DNA template, primer and polymerase exposed to a flow containing only one species of deoxynucleotide at a time. A downstream detection system then determines whether deoxynucleotide is incorporated into the copy or not by detecting the difference in deoxynucleotide concentrations entering and leaving the flow cell containing the complex of DNA template and polymerase.

WO 90/13666 proposes a method directly measuring the growth of the template copy rather than determining it indirectly from compositions in the flow medium. Only one of the four nucleotides is present at a time, and the polymerisation events reflecting the incorporation of a nucleotide or not are detected by spectroscopic means (evanescent wave spectroscopy, fluorescence detection, absorption spectroscopy) or by the individual nucleotides being labelled.

Similar methods employing labelled 3'-blocked deoxynucleotides where the blocking group is removable and which thus permit sequential deoxynucleotide addition/detection steps are disclosed in WO 91/06678, U.S. Pat. No. 5,302,509, DE-A-414 1178 and WO 93/21340. However, the necessary 3'-blocking groups are either not described in any detail, or are not accepted by the required enzyme, or do not permit desired rapid deblocking of the growing template copy strand after each polymerisation event.

One object of the present invention is to provide novel nucleotide derivatives which may be used as chain terminators and which by deprotection may readily be converted into nucleotides or nucleotide analogues that may be further extended.

Another object of the present invention is to provide a method for nucleotide sequence determination using the novel chain terminators.

Still another object of the present invention is to provide a method of synthesizing oligo- or polynucleotides by means of the novel chain terminators.

Another object of the present invention is to provide a process of preparing novel chain terminators according to the invention.

In accordance with the invention, these objects are achieved by the provision of a chain terminating nucleotide or nucleotide analogue having its 3'-hydroxyl group protected by an acetal or thioacetal structure designed in such a way that the 3'-hydroxyl can be deprotected in a relatively short time in dilute acid, such as hydrochloric acid at pH 2, for example.

In one aspect, the present invention therefore provides a compound of the general formula I:

I or a salt thereof, such as a trimethylammonium, ammonium, sodium or potassium salt, wherein B is a nucleobase, X and Z independently are oxygen or sulphur, Y is hydrogen, hydroxy or protected hydroxy, such as methoxy, ethoxy or allyloxy, $R_1$ is hydrocarbyl, which optionally is substituted with a functional group, $R_2$ is hydrogen or hydrocarbyl, which optionally is substituted with a functional group, A is an electron withdrawing or electron donating group capable of moderating the acetal stability of the compound I via $L_1$, $L_1$ and $L_2$ are hydrocarbon linkers, which may be the same or different, $L_2$, when present, being either (i) connected to $L_1$ via the group A, or (ii) directly connected to $L_1$, the group A then being bound to one of linkers $L_1$ and $L_2$, F is a dye label, Q is a coupling group for F, and l, m and n independently are 0 or 1, with the proviso that l is 1 when m is 1, and l is 1 and m is 1 when n is 1.

In Formula I above, the nucleobase B may be natural or synthetic. Natural nucleobases include common nucleobases, such as adenine, guanine, cytosine, thymine and uracil, as well as less common nucleobases, such as xanthine, hypoxanthine or 2-aminopurine. Synthetic nucleobases B are analogues to the natural nucleobases and capable of interacting with other nucleobases in a specific, hydrogen bond determined way.

The hydrocarbyl groups represented by $R_1$ and $R_2$ include a wide variety, including straight and branched chain alkyl, alkenyl, aryl, aralkyl and cycloalkyl, preferably containing up to 10 carbon atoms. Preferred hydrocarbyl groups are primary, secondary or tertiary alkyl, alkenyl or alkynyl groups, especially lower alkyl groups, such as methyl and ethyl. The optional functional group substituents on $R_1$ and $R_2$ are capable of moderating the lability of the 3' acetal group through an inductive effect. Exemplary of such functional groups are tert. amino, nitro, cyano and halogen (fluoride, chloride, bromide, iodide).

Detectable moiety, or label F can be chosen from a vast number of such moieties known to those skilled in the art. Exemplary such moities are radioactively labeled functions, luminescent, electroluminescent or fluorescent labels, and labels that absorb characteristic visible or infrared light. Preferably, F is a fluorescent label.

Coupling group Q, when n=0, is a reactive group to which a label F can be coupled, or, when n=1, is the derivatized residue of a reactive group used for coupling linker $L_2$ to label F. A large number of such coupling groups capable of reacting with and binding label F via a reactive function thereon are known to those skilled in the art. Examples of reactive groups are amino, thio, and carboxyl. In some cases, the group Q is derived completely from the reactive function on the uncoupled F. For example, if the coupling reaction is a substitution reaction, the group reacting with F being, for example, a halogen (fluoride, chloride, bromide or iodide), then the group Q will be represented by the reactive function present on label F.

For certain applications of the compounds of Formula I, as will be described below, no detectable moiety will be needed, and the label F, and optionally also the group Q, can then be omitted.

Electron withdrawing or donating group A is incorporated into the structure as a moderator of acetal stability. The group A may represent a part of the chain $L_1$-A-$L_2$. Representative groups A in that case are amido, sulfoxy, sulfone, carbalkoxy (ester), ether, thioether and amino groups. Alternatively, A may be a side substituent for the $L_1$-$L_2$ chain, representative groups then being, for example, cyano, nitro and halogen (halogen including fluoride, chloride, bromide and iodide). In this latter case, linker $L_1$ will donate structure stretching from the acetal carbon to the place of the substitution, and linker $L_2$ will donate structure stretching from this substitution to the group A. It is to be emphasized that the specific electron withdrawing and electron donating groups mentioned above are only examples and that many more such groups are known and obvious to those skilled in the art.

The structure of hydrocarbon linker $L_1$ will be selected with regard to the function A, inductive effects being highly depending on distance. While a straight aliphatic (saturated or unsaturated) hydrocarbon chain is preferred, branched or cyclic hydrocarbons may be contemplated. Preferably, linker $L_1$ has up to 10 carbon atoms, more preferably up to 6 carbon atoms.

The function of hydrocarbon linker $L_2$ is to provide, together with linker $L_1$, A and coupling group Q, for a sufficiently long distance between the label moiety F and the rest of the compound of Formula I. This is required by spatial preferences of the enzymes (polymerases) for which the compound of Formula I acts as substrate or by the necessity of avoiding interaction between the label and nucleobase B. It is readily understood that the structure of linker $L_2$ highly depends on the particular enzyme, label F and possibly also nucleobase B that are used. A suitable length and structure of linker $L_2$ will therefore be selected by the skilled person for each particular situation. Similarly as for linker $L_1$, a preferred structure for linker $L_2$ is a straight aliphatic (saturated or unsaturated) hydrocarbon chain, although branched or cyclic hydrocarbons may be contemplated. Preferably, linker $L_2$ has up to 10 carbon atoms, more preferably up to 6 carbon atoms.

In cases where the label F and the coupling group Q may be omitted, linker $L_2$ may, of course, also be omitted.

The compounds of Formula I can be deprotected to exhibit a free 3'-hydroxy group in a relatively short time under acidic conditions, e.g. with hydrochloric acid at about pH 2. It is understood that by proper selection of the groups $R_1$, $R_2$, A, $L_1$ and $L_2$ with regard to each other, the deprotection time may be adjusted to a desired range. Under the mentioned acidic conditions, the most preferred compounds of Formula I will be deprotected within, say, 0.01 to 15 minutes.

While the compounds of Formula I may be used as pure chain extension inhibitors, or chain terminators, for example, in DNA sequencing according to the chain termination method, as is per se known in the art, the advantages of the compounds are, of course, better benefited from when the convenient deprotection capabilities of the compounds are utilized. This is, for example, the case when the compounds I are used in nucleic acid sequencing methods based on the sequential incorporation and determination of individual nucleotides in a growing nucleic acid copy strand as described in, for example, the aforementioned WO 91/06678, U.S. Pat. No. 5,302,509, DE-A-414 1178 and WO 93/21340.

Another aspect of the invention therefore provides a method for determining the sequence of a nucleic acid, which method comprises providing a single-stranded template comprising the nucleic acid to be determined, and at least partially synthesizing a complementary nucleic acid molecule in a stepwise serial manner by the addition of nucleotides in which the identity of each nucleotide incorporated into the complementary nucleic acid molecule is determined subsequent to its incorporation, wherein said nucleotides are compounds of Formula I as defined above, and wherein the 3'-blocking group is removed from the nucleotide after its incorporation to permit further extension of the nucleic acid molecule.

In one embodiment, a method for determining the sequence of a nucleic acid comprises the following steps:

(i) providing a single-stranded template comprising the nucleic acid to be sequenced, (ii) hybridising a primer to the template to form a template/primer complex, (iii) subjecting the primer to an extension reaction by the addition of compounds of Formula I with different nucleobases B corresponding the four bases A, C, T and G or analogues thereof, (iv) determining the type of the compound of Formula I added to the primer, (v) selectively hydrolysing the acetal protective group, and (vi) repeating steps (iii) to (v) sequentially and recording the order of incorporation of compounds of Formula I.

The different compounds of Formula I in step (iii) may be added in sequence, in which case the four different compounds I may carry the same label F. Alternatively, the different compounds I have different labels F and are added at the same time.

In a preferred embodiment of the method of the invention, the template/primer complex is bound to a solid-phase support, such as a sequencing chip, for example. The template may be attached to the solid support via a binding linker, which, for instance, is ligated to the 5'-end of the template or incorporated in one of the ends of the template by polymerase chain reaction (PCR). The binding linker may then be attached to the solid support by use of a streptavidin coupling system. Alternatively, the primer may be attached to the solid support.

The compounds of Formula I may, of course, also conveniently be used in so-called mini-sequencing (see e.g. Syvänen A-C et al., Genomics 8:684–692 (1990).

As is readily understood by a person skilled in the art, the compounds of Formula I may also be used in the synthesis of nucleotide chains, and another aspect of the invention relates to such use. For example, oligonucleotides and polynucleotides may be prepared by successively coupling compounds of Formula I to each other in any desired base order with intervening deblocking and using a non-template dependent polymerase, such as a terminal transferase. For such synthesis, the groups $L_2$, Q and F in Formula I may, of course, be omitted.

The compounds of Formula I may be prepared by methods known per se. In a further aspect, however, the invention provides a particular method for the preparation of a subgroup of compounds of Formula I by direct 3'-OH protection, and more particularly compounds of Formula Ia:

Ia or a salt thereof, wherein B, X, Z, $R_1$, $R_2$, Q, F, m and n are as defined above, and p and q independently are integers from 1 to 10, preferably from 1 to 6, by reacting a compound of Formula II:

II or a salt thereof, wherein B and X are as defined above, with a compound of Formula III:

III wherein $R_1$, $R_2$, Z and p are as defined above, and $R_3$ is hydrocarbyl (for example, as defined for $R_1$ and $R_2$ above), to produce a compound of Formula IV:

IV or a salt thereof, wherein B, X, Z, $R_1$, $R_2$, $R_3$ and p are as defined above, optionally reacting the latter with a diamine $H_2N$—$(CH_2)_q$—$NH_2$, wherein q is as defined above, to produce a compound of Formula V:

wherein B, X, Z, $R_1$, $R_2$, p and q are as defined above, and optionally coupling a dye label F to the terminal amino group.

In the following, the invention will be illustrated by some non-limiting examples. Reference will be made to the accompanying drawings, wherein.

EXAMPLE 1

Figure 1:
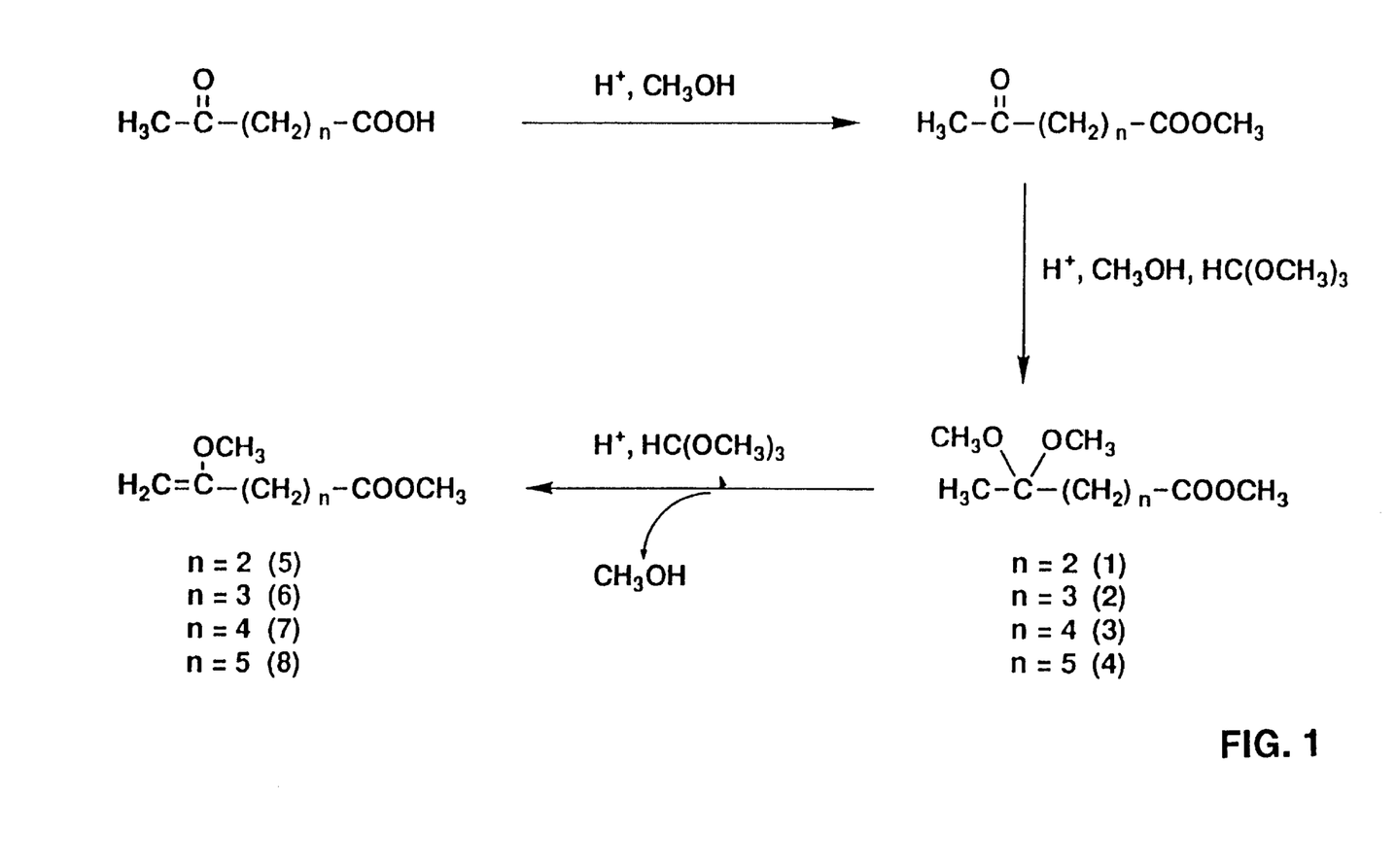
FIG. 1 is a reaction scheme for the enolether synthesis described in Example 1 below. Intermediate and final products corresponding to various values of integer "n" in the respective structural formulae are identified by numbers indicated within brackets after the n-values listed under the respective formulae.

Synthesis of Enolethers for Derivatization of Nucleotide Triphosphates (FIG. 1)

Step 1. Esterification of ketoacids

The appropriate ketoacid (1 eq) was added at once to a large excess of dry methanol (20 eq), previously treated with thionyl chloride (0.1 eq). The homogenous mixture was refluxed overnight, evaporated under reduced pressure, and partitioned between saturated sodium hydrogen carbonate and dichloromethane. The combined organic extracts were dried with magnesium sulphate, evaporated and the residue was distilled under reduced pressure to give the appropriate methyl ester in a high yield (80% to 95%).

The following ketoacids were used:

1) 4-oxy pentanoic acid (levulinic acid) (Aldrich)
2) 5-oxy hexanoic acid has not been isolated. Instead a commercial ethyl ester-derivative of this acid (Merck) was transesterified in a reaction analogous to the above general procedure.
3) 6-oxy heptanoic acid was obtained from 2-methyl cyclohexanol (Merck), according to a published procedure (Org. Synth. 31: 3–5, (1951)).
4) 7-oxy octanoic acid was obtained from 2-acetyl cyclohexanone as described (J. Am. Chem. Soc. 70:4023–4026 (1948)).

Step 2. Synthesis of the dimethoxyacetal derivatives (compounds 1–4 in FIG. 1)

Benzenesulfonic acid (0.01 eq) was added to each of above methyl esters (1 eq) dissolved in methanol (2 eq) and trimethylorthoformate (3 eq). The dark brown mixture was refluxed for 3 h, neutralized by addition of dry triethylamine (0.1 eq), and evaporated. The residue was distilled under lowered pressure to yield a pure acetal.

Compound 1. The physical and NMR data for this acetal correspond well to the data reported previously.

Compound 2. Yield 85%, bp. 120° (15 mm Hg) $^1$H NMR (CDCl$_3$): 1.28 (s, 3 H), 1.60–1.69 (m, 4 H), 2.34 (t, 2 H), 3.17 (s, 6 H), 3.67 (s, 3 H).

Compound 3. Yield 92%, bp. 130–133° (15 mm Hg) $^1$H NMR (CDCl$_3$): 1.25 (s, 3 H), 1.29–1.35 (m, 2 H), 1.60–1.70 (m, 4 H), 2.33 (t, 2 H), 3.17 (s, 6 H), 3.67 (s, 3 H).

Compound 4. Yield 87%, bp. 147–149° (15 mm Hg) $^1$H NMR (CDCl$_3$): 1.25 (s, 3 H), 1.27–1.38 (m, 4 H), 1.57–1.67 (m, 4 H), 2.31 (t, 2 H), 3.16 (s, 6 H), 3.66 (s, 3 H).

Step 3. Synthesis of enolethers (compounds 5–8 in FIG. 1).

A mixture of the appropriate acetal (1 eq) and trimethylortoformate (0.5 eq) was placed in a distillation flask, equipped with a 20 cm Vigreux column. Benzenesulfonic acid (0.02 eq) was added and the mixture was refluxed. The heating was regulated so that the liberated methanol evaporated slowly. After 4 h the heating was increased and the dark mixture was fractionated under reduced pressure without previous neutralization of the acidic catalyst. The yields of isolated colorless enolethers were in all cases very high (85–95%) but GC and NMR analyses showed the presence of starting acetal in proportions from 10 to 30%. Since these impurities were not expected to influence the derivatization of nucleotides no attempts were made to purify them further. The complete assignment of NMR signals was difficult because of the presence of starting material and the fact that these asymmetric enolethers exist as several isomeric forms. Nevertheless, in all spectra a vinylic signal of CH$_2$ from one isomer at around 4.4 to 4.5 ppm and a vinylic signal of CH from the other isomer at 3.85 ppm could be easily observed.

EXAMPLE 2

Figure 2:
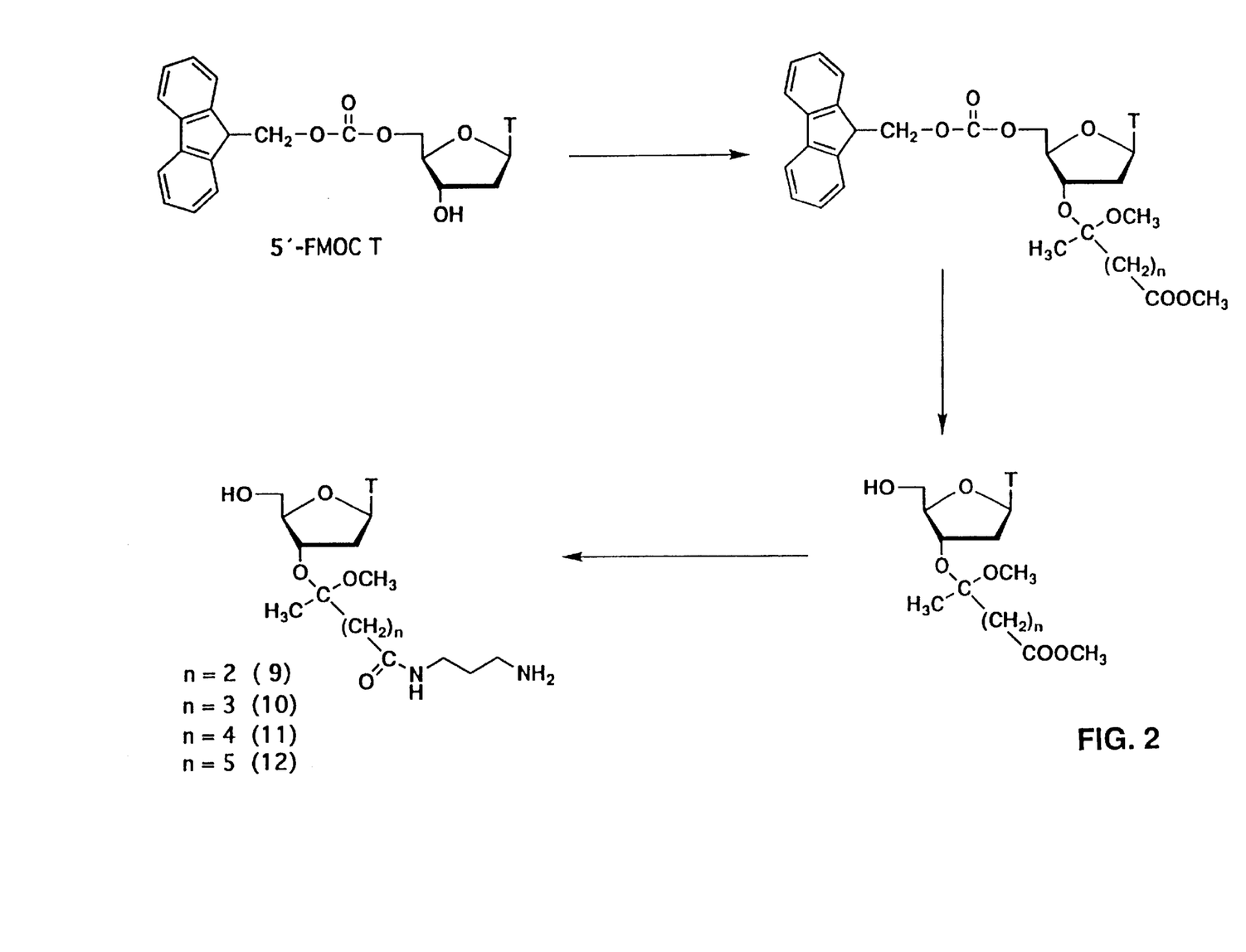
FIG. 2 is a reaction scheme for the preparation of 3'-acetal-modified thymidine described in Example 2 below. Prepared final compounds corresponding to various values of integer "n" in the respective structural formula are identified by numbers indicated within brackets after the n-values listed under the formula.

Synthesis of 3' Acetal-modified Thymidine (FIG. 2)

The 5'-protected thymidine, 5'-FMOC T (FMOC-fluorenyl methoxycarbonyl), (116 mg, 0.25 mmol) was dried by coevaporation with dry acetonitrile (10 ml) and dissolved in dry dioxane (5 ml). To this magnetically stirred solution an appropriate enolether (0.5 ml, ≈10 eq) prepared in Example 1 was added, followed by trifluoroacetic acid (20 ml, 1 eq). After 45 min, the TLC analysis (Silicagel 60 F254, 10% methanol in chloroform) showed complete consumption of the starting material, and dry triethylamine (2 ml) was introduced in order to remove the base-labile FMOC-group. After this process was completed (60 min), the whole mixture was evaporated under reduced pressure. The nucleoside was separated from the excess of enolether by precipitation from petroleum ether, and the precipitate, dissolved in 5 ml of dry methanol, was treated with 1,3-diaminopropane (2 ml, 100 eq) at 60° for 180 min in order to effect the aminolysis of the ester function on the acetal moiety. Finally, the reaction mixture was evaporated under low pressure (oil pump) and the crude material was flash chromatographed on a silica gel column, equilibrated in ethanol and using a step gradient of conc. ammonium hydroxide (0–10%) in ethanol. The material, homogeneous by TLC (developed in 1-butanol-ammonium hydroxide 8:2), was combined, evaporated, and coevaporated with toluene, to give the NMR pure product (compounds 9–12 in FIG. 2) in high yield (72 to 85%). The pure material was stored as a stock solution in methanol after addition of three drops of ammonia.

EXEMPLE 3

Figure 3:
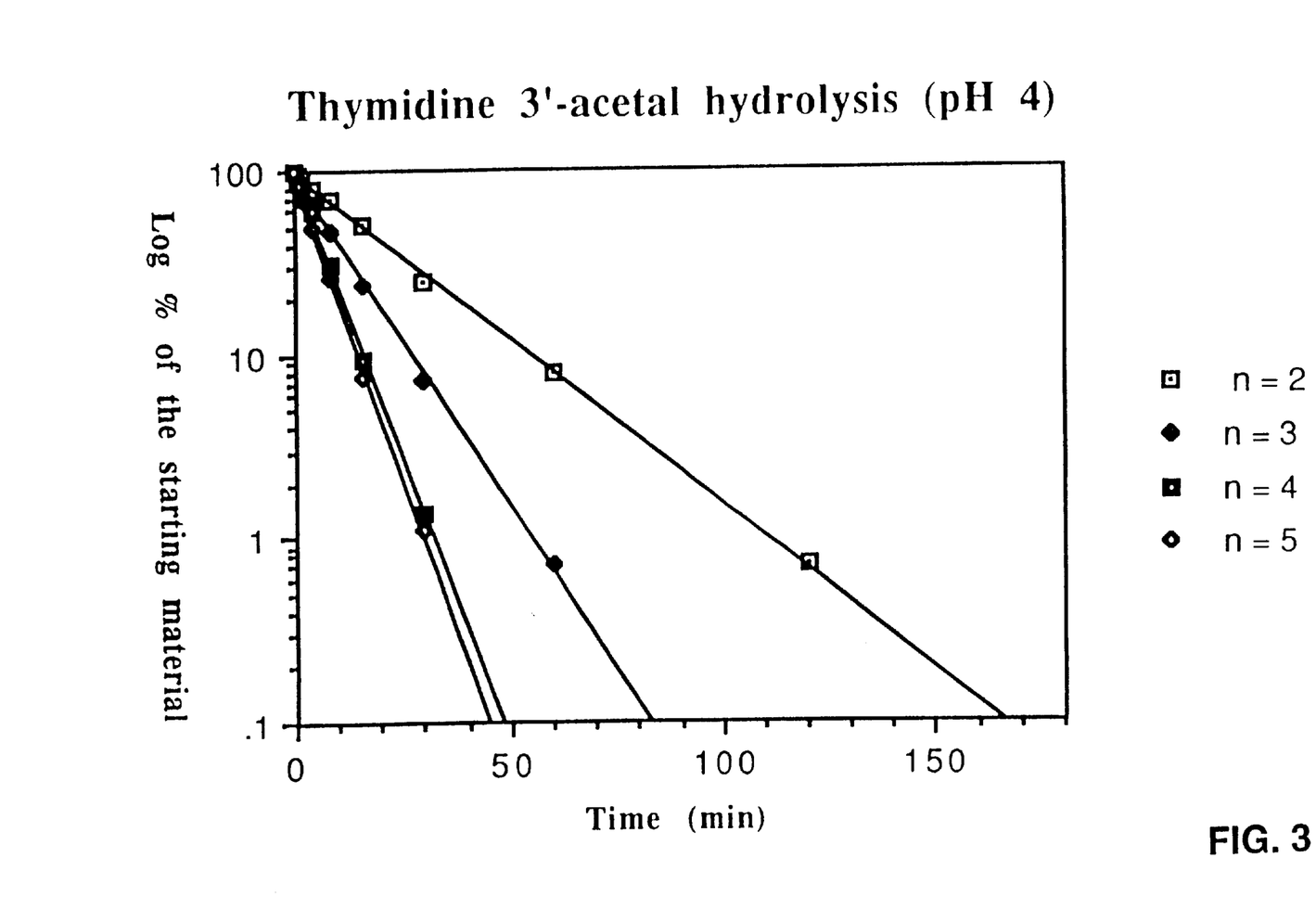
FIG. 3 is a graph showing thymidine 3'-acetal hydrolysis at pH 4 as log % of remaining acetal versus time in minutes.

Acidic Hydrolysis (pH 4) of Thymidine, Substituted at the 3'-Position with Different Acetyl Groups A reference acetate buffer pH 4.0, prepared by mixing of solutions of sodium acetate (0.20 M, 18.0 ml) with acetic acid (0.20 M, 82.0 ml) was used in all hydrolysis studies. To this buffer (10.0 ml) an ethanolic solution of the appropriate thymidine 3'-acetal derivative prepared in Example 2 (compounds 9–12 in FIG. 2) (100 ml) was added with gentle stirring. At different time points a sample of 0.5 ml was withdrawn and placed in a tube containing 15 ml of conc. ammonia to raise the pH to 9. Samples were analyzed by FPLC using an anion exchange column (Mono Q-Pharmacia Biotech AB) and a gradient system of tetraethylammonium bicarbonate pH 8.2 for elution (0.05 to 0.75 M). The peak areas of starting material and its hydrolysis product thymidine were integrated, and plotted as shown in FIG. 3.

EXAMPLE 4

Figure 4:
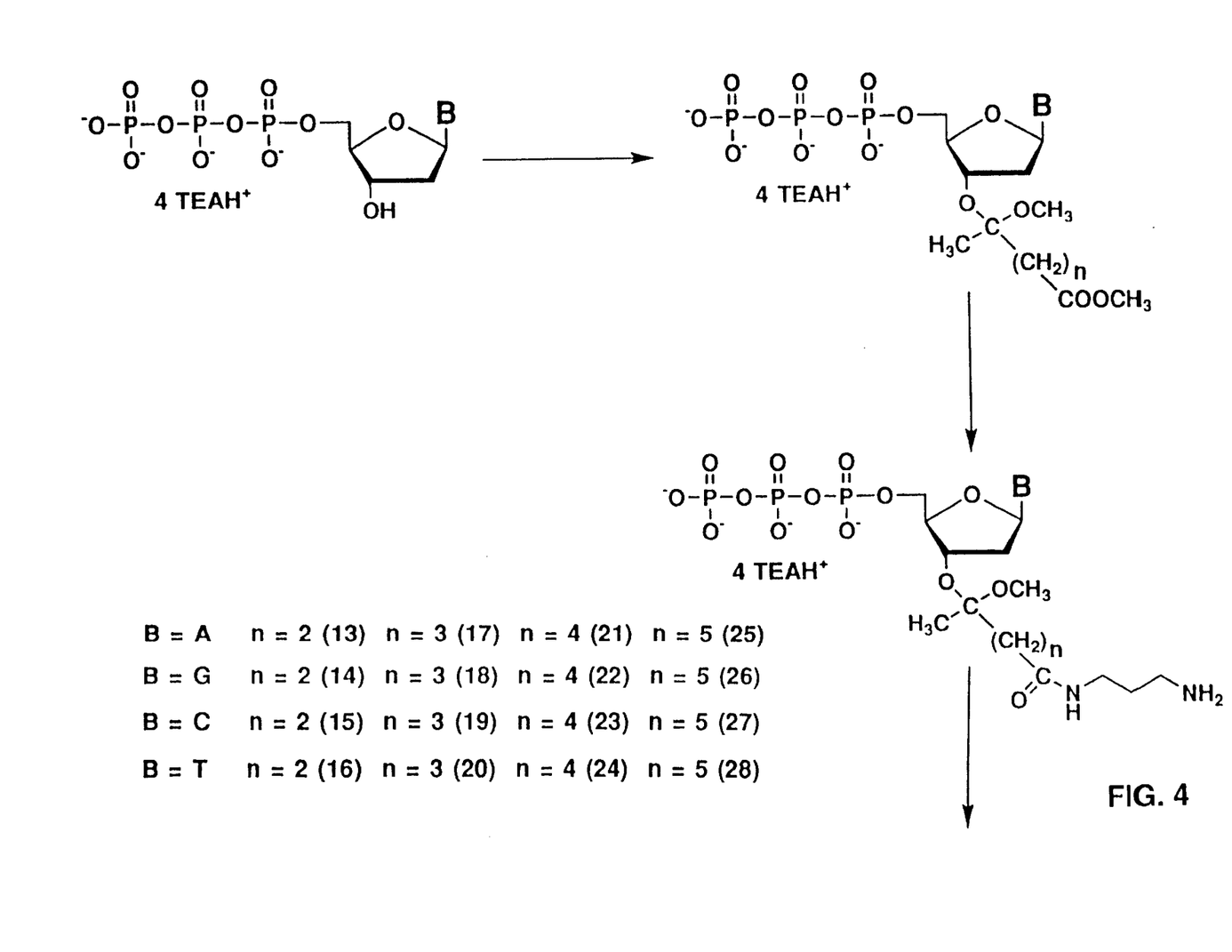
FIG. 4 is a reaction scheme for the one-pot synthesis of 3'-acetal protected deoxynucleotide triphosphates described in Example 4 below. Intermediate and final products corresponding to various values of integer "n" in the respective structural formulae are identified by numbers indicated within brackets after the n-values listed under the respective formulae.

One Pot-synthesis of Deoxynucleotide Triphosphates, Protected at their 3'-OH Position by a Functionalized Acetal Group (FIG. 4)

A commercial deoxynucleotide triphosphate (pppdT, pppdC, pppdG, or pppdA) was chromatographed on a preparative Mono Q column using a gradient system of tetraethylammonium bicarbonate pH 8.2 (0.05 to 1.3 M) to obtain the pure triphosphate in the form of a triethylammonium salt. This material was evaporated on a Rotavapor, coevaporated with dry acetonitrile (3×2 ml), and dissolved in molecular sieve-dried trimethylphosphate (0.5 ml). The appropriate enolether (compounds 5–8 in FIG. 1) (0.2 ml) and trifluoroacetic acid (10 eq as a 10% solution in dry dioxane) were added. The homogeneous mixture was incubated at 20° C. for 60 min, neutralized by the addition of triethylamine (100 ml), and precipitated from a 1:1 mixture of petroleum ether and diethyl ether. The oily precipitate was dissolved in methanol (2 ml) and 1,3-diaminopropane (0.5 ml) or another diamine (1,4-diaminobutane, 1,6-diaminohexane) (0.5 ml) was added. The ester function was subjected to aminolysis overnight at 60° C. The mixture was again precipitated from 1:1 petroleum ether and diethyl ether, washed with diethyl ether, and dissolved in water. The water solution was analyzed and preparatively purified on the described anion exchange column. The well resolved products (compounds 13–28 in FIG. 4) always appear prior to the original deoxynucleotide triphosphate, having a retention time comparable to that of the appropriate deoxynucleotide diphosphate (as was found from separate coinjection experiments). An aliquot of the isolated 3'-acetal-modified derivative was evaporated, treated with 80% acetic acid for 2 min, and, after evaporation of acid, reinjected to the same chromatographic system. In all cases all starting material was reacted and a single product with higher retention time was formed that corresponded to the original deoxynucleotide triphosphate. Thymidine triphosphate reacts to form, besides the desired 3'-modified derivative, also another product with even shorter retention time but that also hydrolyses to the starting triphosphate during acid treatment. It is assumed that this product is the bis-3'-O, 4-O-acetal-derivative of thymidine triphosphate. This type of side products was not present in reactions that used other nucleotide triphosphates. It should also be stressed that very little products of depurination were formed in reactions in which pppdG and pppdA were used. This can be explained by the mild acid applied as a catalyst, the large excess of enolether used in the reaction, and the fact that the bases existed in an unprotected (more acid resistant) form.

EXAMPLE 5

Coupling of a Fluorophore to the 3'-Functionalised Deoxynucleotide Triphosphate (FIG. 4)

This derivatization can be performed with a variety of reactive fluorophores that may differ in their reactivity and in their optimal reaction conditions. Here is described the procedure for labelling of 3'-functionalized deoxynucleotide triphosphate with fluorescein isothiocyanate.

The appropriate nucleotide triphosphate, possessing an amino group attached to the 3'-position of the sugar residue via an acetal function (compounds 13–28 in FIG. 4), was evaporated and dissolved in 0.1 M carbonate buffer pH 10 (0.5 ml). Fluorescein isothiocyanate (single isomer) (10 eq), dissolved in dimethylformamide (0.25 ml), was added and the mixture was incubated overnight at 20° C. The reaction mixture was applied on a prototype FPLC Superdex® gel filtration column (Pharmacia Biotech AB) (equivalent to Sephadex® G-10; Pharmacia Biotech AB), equilibrated and run in TEA $HCO_3$ buffer (0.1 M). The fluorescent material appearing in the void was collected (compounds 29–44 in FIG. 4). As expected, the original deoxynucleotide triphosphate was formed upon action of acid on the fluorescein-labelled nucleotide.

EXAMPLE 6

Stepwise Enzymatical Incorporation of 3'-Modified Triphosphates

Four oligonucleotides were prepared, having sequences corresponding to the M13 sequencing primer, and designed to incorporate to their 3'-ends T, G, A or C base respectively:
(T) 5'CGACGTTGTAAAACGACGGCCAG (SEQ ID NO:1) (23 mer)
(G) 5'CGACGTTGTAAAACGACGGCCA (SEQ ID NO:2) (22 mer)
(A) 5'CGACGTTGTAAAACGACGGCC (SEQ ID NO:3) (21 mer)
(C) 5'CGACGTTGTAAAACGACGGC (SEQ ID NO:4) (20 mer)

Each of them was radioactively labelled with $^{32}P$ using T4 polynucleotidekinase.

In order to investigate if the modified nucleotide triphosphates are accepted effectively and specifically by the T7 polymerase, each of the labelled primers was subjected to the single step extension conditions. These reaction mixtures (20 ml) were composed of the respective primer (0.1 pmol), M13 template (1 pmol), and 3'-modified thymidine triphosphate (compound 16 in FIG. 4) in a buffer system pH 7.5 containing Tris/HCl (40 mM), $MnCl_2$ (4 mM), dithiothreitol (DTT) (11 mM), sodium isocitrate (29 mM) and sodium chloride (23 mM). The mixtures were denatured at 70° C., cooled, and incubated at 42° C. after the addition of T7 DNA polymerase (10 U) for 30 min. All reactions were stopped by addition of formamide (20 ml), denatured at 70° C., cooled on ice, and separated on a 6% denaturing sequencing gel. The developed autoradiogram showed that one-base extension had taken place solely in the reaction containing 23-mer-T (designed to prime the M13 template and incorporate thymidylic acid at its 3'-end). None of the other reactions containing primers designed for incorporation of dG, dA and dC, respectively, showed any sign of primer extension.

EXAMPLE 7

Sequencing Reaction with Modified Chain Terminator

All sequencing reactions were performed according to the standard ABI protocol (Taq Dye Primer Cycle Sequencing Kit—protocol 901482).

The sequencing reactions consisted of the following components: M13 mp 18 ss-DNA template (1 pmol), 5'-fluorescein labelled universal primer (1 pmol, Pharmacia Biotech AB), Ampli Taq DNA polymerase (4U) and T-termination mixture in cycle sequencing buffer (Tris-HCl pH 8.9, 80 mM, ammonium sulfate 20 mM, magnesium chloride 5 mM). Instead of the standard ddT triphosphate, compound 16 in FIG. 4, in different proportions with TTP, was used as a chain terminator. After the cycling was completed, an equal volume of formamide was added and the mixture was heated for 2 min at 90° C., cooled on ice and loaded onto 6% acrylamide urea gel. Separation and analysis of products were performed on an A.L.F. DNA-sequencer (Pharmacia Biotech AB).

As a result, a pattern of fluorescent-labelled sequences was obtained. This electrophoretic picture was specific for the applied terminator.

What is claimed is:

1. A compound of the structure I:

$$\text{HO}-\overset{\overset{O}{\|}}{\underset{OH}{P}}-O-\overset{\overset{O}{\|}}{\underset{OH}{P}}-O-\overset{\overset{X}{\|}}{\underset{OH}{P}}-O-\underset{\underset{\underset{R_2}{|}}{\underset{R_1-Z-C-L_1-(A)-(L_2)_l-(Q)_{\overline{m}}-(F)_n}{|}}}{\overset{B}{\underset{O}{\bigcirc}}\underset{Y}{|}}\quad\text{I}$$

Or a salt thereof, wherein

B is a nucleobase,

X and Z independently are oxygen or sulphur,

Y is hydrogen or a protected or unprotected hydroxy, $R_1$ is hydrocarbyl, which optionally is substituted with a functional group selected from the group consisting of tertiary amino, nitro, cyano and halogen, $R_2$ is hydrogen hydrocarbyl, which optionally is substituted with a functional group selected from the group consisting of tertiary amino, nitro, cyano and halogen, A is an electron withdrawing or electron donating group capable of moderating the acetyl stability of the compound I, $L_1$ and $L_2$ are hydrocarbon linkers, which may be the same or different, $L_2$, when present, being either (I) connected to $L_1$ via the group A, or (ii) directly connected to $L_1$, the group A then being connected to one of linkers $L_1$ and $L_2$, F is a dye label, Q is a coupling group for F, and l, m and n independently are 0 or 1, with the proviso that l is 1 when m is 1, and l is 1 and m is 1 when n is 1.

2. The compound according to claim 1, wherein $R_1$ and $R_2$ are independently primary, secondary or tertiary alkyl, optionally substituted with one or more functional groups selected from the group consisting of tertiary amino, nitro, cyano and halogen.

3. The compound according to claim 2, wherein $R_1$ and $R_2$ are methyl or ethyl.

4. The compound according to claim 1, 2 or 3, wherein A is a part of a chain $L_1$-A-$L_2$ and is amido, sulfoxy, sulfone, carbolkoxy, ether, thioether or amino.

5. The compound according to claim 1, 2 or 3, wherein A is a substituent to a chain $L_1$-$L_1$ and is cyano, nitro or halogen.

6. The compound according to claim 1, wherein $L_1$ is a straight aliphatic hydrocarbon chain, having up to 10 carbon atoms.

7. The compound according to claim 1, wherein $L_2$ is a straight aliphatic hydrocarbon chain, having up to 10 carbon atoms.

8. The compound according to claim 1, wherein Y is alkoxy.

9. A method for determining the sequence of a nucleic acid, comprising providing a single-stranded template comprising the nucleic acid to be determined, and at least partially synthesizing a complementary nucleic acid molecule in a stepwise serial manner by the addition of nucleotides in which the identity of each nucleotide incorporated into the complementary nucleic acid molecule is determined subsequent to its incorporation, wherein said nucleotides are compounds of Formula I as defined in claim 1, and wherein the 3'-blocking group is removed from the nucleotide after its incorporation to permit further extension of the nucleic acid molecule.

10. The method according to claim 9, wherein the 3'-blocking group is removed by acid hydrolysis.

11. The method according to claim 9 or 10, wherein F in Formula I is a fluorescent label.

12. The method according to claim 9, wherein said single-stranded template is bound to a solid support.

13. A process of preparing a compound of Formula Ia:

$$\text{HO}-\overset{\overset{O}{\|}}{\underset{OH}{P}}-O-\overset{\overset{O}{\|}}{\underset{OH}{P}}-O-\overset{\overset{X}{\|}}{\underset{OH}{P}}-O-\overset{B}{\underset{\underset{R_2}{|}\underset{(CH_2)_p}{|}}{\underset{\underset{O}{\|}\underset{H}{|}}{C-N-(CH_2)_{\overline{q}}-(Q)_{\overline{m}}-(F)_n}}}{\overset{O}{\bigcirc}\underset{C-ZR_1}{|}}\quad\text{Ia}$$

ar a salt thereof, wherein B, X, Z, $R_1$, $R_2$, Q, F, m and n are as defined in claim 1, and p and q independently are integers from 1 to 10, by reacting a compound of Formula II:

$$\text{HO}-\overset{\overset{O}{\|}}{\underset{OH}{P}}-O-\overset{\overset{O}{\|}}{\underset{OH}{P}}-O-\overset{\overset{X}{\|}}{\underset{OH}{P}}-O-\overset{B}{\underset{OH}{\bigcirc}}\quad\text{II}$$

or a salt thereof, wherein B and X are as defined above, with a compound of Formula III:

$$R_2-\underset{\underset{ZR_1}{|}}{C}=CH-(CH_2)_{p-1}-COOR_3\quad\text{III}$$

wherein $R_1$, $R_2$, Z and p are as defined above, and $R_3$ is hydrocarbyl, to produce a compound of Formula IV:

IV or a salt thereof, wherein B, X, Z, $R_1$, $R_2$, $R_3$ and p are as defined above, optionally reacting the latter with a diamine $H_2N$—$(CH_2)_q$—$NH_2$, wherein q is as defined above, to produce a compound of Formula V:

V wherein B, X, Z, $R_1$, $R_2$, p and q are as defined above, and optionally coupling a dye label F to the terminal amino group.

14. A method of synthesizing nucleic acid oligo or polynucleotides comprising adding a compound of claim 1 to a nucleic acid synthesis reaction under conditions effective to incorporate said compound into said oligo-or polynucleotide.

15. The compound according to claims 1 or 2, wherein said halogen is selected from the group consisting of fluoride, chloride, bromide, and iodide.

* * * * *

```
                         SEQUENCE LISTING

<160> NUMBER OF SEQ ID NOS: 4

<210> SEQ ID NO 1
<211> LENGTH: 23
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 1
cgacgttgta aaacgacggc cag                                            23

<210> SEQ ID NO 2
<211> LENGTH: 22
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 2
cgacgttgta aaacgacggc ca                                             22

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 3
cgacgttgta aaacgacggc c                                              21

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 4
cgacgttgta aaacgacggc                                                20
```